(12) United States Patent
Bodden et al.

(10) Patent No.: US 8,691,299 B2
(45) Date of Patent: Apr. 8, 2014

(54) INGESTIBLE INSECT REPELLENT COMPOSITION AND SYSTEM

(76) Inventors: Deveral Bodden, Carolina, PR (US); Ana Carro, Ponce, PR (US)

( * ) Notice: Subject to any disclaimer, the term of this patent is extended or adjusted under 35 U.S.C. 154(b) by 229 days.

(21) Appl. No.: 13/079,410

(22) Filed: Apr. 4, 2011

(65) Prior Publication Data

US 2012/0251640 A1   Oct. 4, 2012

(51) Int. Cl.
*A61K 36/534* (2006.01)
*A61K 36/00* (2006.01)

(52) U.S. Cl.
USPC ........... 424/747; 424/725; 514/168; 514/167; 514/251; 514/276; 514/256; 514/474

(58) Field of Classification Search
USPC .......... 424/725, 747; 514/168, 167, 251, 276, 514/256, 474
See application file for complete search history.

(56) References Cited

U.S. PATENT DOCUMENTS 6,187,318 B1 * 2/2001 Mitchell et al. ............... 424/735
2006/0171993 A1 * 8/2006 Barrett-Reis et al. ......... 424/439

* cited by examiner

*Primary Examiner* — Patricia Leith
(74) *Attorney, Agent, or Firm* — Luis Figarella

(57) ABSTRACT

Disclosed is an ingestible insect repellent composition and method utilizing a mixture of vitamins and extracts of lemon, coffee and/or peppermint as active insect deterrent. The composition may be diluted for easier intake into water, juices, milk, soda, mixed drinks and other beverages. Exemplary embodiments disclosed herein may include creating a premix capable of providing up to 100% of the suggested daily intake of specific Vitamin when diluted in any appropriate beverage. Exemplary embodiments may be utilized to repel insects for hours after ingestion in both humans and animals. The exemplary embodiments may provide this repellant without the harmful effects of other chemicals and repellants.

7 Claims, 1 Drawing Sheet

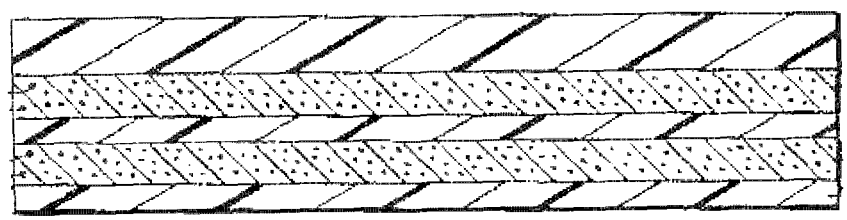
PRIOR ART ns. In one
INGESTIBLE INSECT REPELLENT COMPOSITION AND SYSTEM

PATENTS CITED

The following documents and references are incorporated by reference in their entirety, Mills (US Pat. Pub. No. 2007/0092544) and Enscore et al (U.S. Pat. No. 4,559,222).

TECHNICAL FIELD

The present invention generally relates to the field of insect repellents, and in particular to an ingestible insect repellant composition, system and method which is safe for ingestion by humans and animals, yet allows for the secretion through the skin of an agent effective in repelling insects.

DESCRIPTION OF THE RELATED ART

Most insect repellents use chemicals that may be harmful to humans and animals. Even when they are 'naturally derived', the delivery method for them tend to rely heavily in intrusive mixtures or atomizers. These chemicals and their delivery method sometimes have harmful effects upon humans, animals, and other. What is needed is repellent that utilizes natural ingredients that may be ingested by a human or animals as part of their everyday activities (preferably with additional vitamins and nutrients), such that its use (and benefits) becomes part of everyday life, and occurs without harmful effects.

SUMMARY OF THE INVENTION

This section is for the purpose of summarizing some aspects of the present invention and to briefly introduce some preferred embodiments. Simplifications or omissions may be made to avoid obscuring the purpose of the section. Such simplifications or omissions are not intended to limit the scope of the present invention.

The present invention is for an ingestible insect repellent composition and method utilizing a mixture of vitamins and extracts of lemon, coffee and/or peppermint as active insect deterrent. The composition may be diluted for easier intake into water, juices, milk, soda, mixed drinks and other beverages. Exemplary embodiments disclosed herein may include creating a premix capable of providing up to 100% of the suggested daily intake of specific Vitamin when diluted in any appropriate beverage. Exemplary embodiments may be utilized to repel insects for hours after ingestion in both humans and animals. The exemplary embodiments may provide this repellent without the harmful effects of other chemicals and repellents.

In one aspect the invention comprises an ingestible insect repellent composition comprising a transfer agent, representing 90 to over 99% of the composition, said transfer agent being non-toxic to humans and capable of crossing the dermis of humans and similar animals and being secreted as part of the sweating function, and a catalyst group comprised of one or more B-complex vitamins, said catalyst group representing the balance of the totality of the above composition. In one aspect, the transfer agent is comprised of extracts made from lemon, coffee, peppermint leaf, Achillea alpine, alpha-tyerpinene, basil, callicarpa Americana or Beautyberry, Camphor, castor oil, Catnip, cedar oil, celery extract, cinnamon, clove, fennel, garlic, geranium, lavender, lemongrass, marigold, rosemary or thyme. The catalyst group is selected in various percentages from the group comprised by the B-complex vitamins.

In one aspect, the catalyst group is comprised of equal portions of $B_1$ and $B_{12}$ vitamins. In another aspect, the catalyst group is comprised of equal portions of $B_1$, $B_2$ and $B_6$ vitamins. In another aspect, the catalyst group is comprised of equal portions of $B_1$, $B_2$, $B_6$ and $B_{12}$ vitamins. In yet another aspect, the proportions of the catalyst group are varies by as much as 50% from one to another. In another aspect, the composition has amounts of Vitamins $B_3$, $B_5$, $B_7$, $B_9$ and Vitamin C sufficient to meet the recommended USDA minimums for an adult. In yet another aspect, sufficient fluid to dilute said composition into a drinkable mix is added.

In one aspect, the invention comprises an ingestible insect repellent for humans or animals comprising blending a transfer agent with one or more components selected from a catalyst group comprised of the B-complex vitamins. In one aspect, the blending transfer agent is selected from the group comprised from the following extracts, lemon, coffee, peppermint leaf, Achillea alpine, alpha-tyerpinene, basil, callicarpa Americana or Beautyberry, Camphor, castor oil, Catnip, cedar oil, celery extract, cinnamon, clove, fennel, garlic, geranium, lavender, lemongrass, marigold, rosemary or thyme.

In another aspect, the catalyst group is selected from a group comprised of equal portions of $B_1$, $B_2$, $B_6$ and $B_{12}$ vitamins. In yet another aspect, the proportions of the catalyst group are varies by as much as 50% from one to another. In another aspect, the composition has amounts of Vitamins $B_3$, $B_5$, $B_7$, $B_9$ and Vitamin C sufficient to meet the recommended USDA minimums for an adult. In another aspect, the catalyst group is selected from a group comprised of the $B_1$, $B_2$ and $B_6$ vitamins, the $B_1$ and $B_2$ vitamins. In an other aspect, the invention is a method for preparing an ingestible insect repellent for humans or animals comprising blending a transfer agent with one or more components selected from a catalyst group; and ingesting said repellent.

Other features and advantages of the present invention will become apparent upon examining the following detailed description of an embodiment thereof, taken in conjunction with the attached drawings.

BRIEF DESCRIPTION OF THE DRAWINGS

FIG. 1 shows an illustration of a transdermal patch in the Prior Art.

DETAILED DESCRIPTION OF THE PREFERRED EMBODIMENT

To provide an overall understanding of the invention, certain illustrative embodiments and examples will now be described. However, it will be understood by one of ordinary skill in the art that the same or equivalent functions and sequences may be accomplished by different embodiments that are also intended to be encompassed within the spirit and scope of the disclosure. The compositions, apparatuses, systems and/or methods described herein may be adapted and modified as is appropriate for the application being addressed and that those described herein may be employed in other suitable applications, and that such other additions and modifications will not depart from the scope hereof.

The present invention accomplishes an ingestible insect repellent system for humans or other animals capable of sweating or otherwise transferring elements in their bloodstream through their skin, dermis, hide or similar body barrier to the outside. While a deterrent to many insects, such an outgoing transdermal delivery method is particularly effective when fighting mosquitoes and other flying insects that intent to byte their victim's skin.

Most of us are very familiar with transdermal patches designed to infuse medication into the blood stream. FIG. 1 illustrates such a patch structure, according to the Prior Art disclosure in Enscore et al (U.S. Pat. No. 4,559,222). In their various embodiments, such patches pass a certain element, component or combination of them through the skin layer, into the bloodstream. In this fashion, medication can be administered to a user externally.

The invention described here does the opposite, it takes into the body one or more agents that have been found to have insect repellent qualities, and by combining them with a number of catalysts that facilitate body actions such as circulation, achieves a formulation that will encourage the transfer of the repellent agent from the user's bloodstream to their skin surface, from where the natural evaporation or sublimation of the agent in the user's skin provides for its action as a repellent.

The transfer agent goes through the skin or dermis (that of the skin allowing various substances to cross it), but in the opposite direction. That is, the user ingests an agent, element, or combination of agents that they will then exude in combination with their perspiration, sweat or other fluid transfer to the skin. This fluid secretion by the skin is common in mammals as a cooling mechanism. Even in some animals with no sweat gland, it is common for fluids to be secreted through their mouth.

In short, the disclosed system allows for a non-toxic repellent to be "sweated" (although in reality it the repellent transfer agent mixed with the other common components in sweat that is passed through the dermis and fairly evenly distributed into the skin. A common reaction to sweating, is to use the palms of our hands to distribute it along the skin (as well as to say, "phew, its hot", although the latter has no contribution to the repellent action), this spreading of the sweat, does has the effect of coating any area of the body that has not had any repellent coverage, increasing it's effectiveness.

The first element the ingestible repellent system requires, is a suitable transfer agent (any of a number of substances that are capable of traveling across the dermis from the bloodstream) that is safe to be ingested by the user. This transfer agent(s) must be completely safe to the human or animal performing the ingesting, while at the same time being capable of being exuded through the dermis. This, inside-out, repellent application is primarily accomplished by the transfer agent. The transfer agent may be comprised of one or a combination of the following elements; lemon, coffee or peppermint.

When we refer to the lemon, we are not referring to the small evergreen tree (Citrus×limon, often given as C. limon) native to Asia, but to said tree's oval yellow fruit. The fruit is used for culinary and non-culinary purposes throughout the world, primarily for its juice, though the pulp and rind (zest) are also used in cooking and baking. Lemon juice is about 5% to 6% (approximately 0.3 M) citric acid, which gives lemons a sour taste, and a pH of 2 to 3. This makes lemon juice an inexpensive, readily available acid for use in educational science experiments. Many lemon-flavored drinks and candies are available, including lemonade and sherbet lemons. In one embodiment, the extract of said lemon juice is used, in concentrations of at least 10:1.

Coffee is a brewed drink prepared from roasted seeds, called coffee beans, of the coffee plant. These beans are the seeds of coffee cherries that grow on said tree. Coffee has a stimulant effect, and can have a stimulating effect on humans due to its caffeine content. However, applicant's experiments have shown positive results with both Caffeinated and Decaffeinated coffee extracts. In one embodiment, the extract of said coffee is used in concentrations of at least 10:1.

Peppermint (Menthe×pipe Rita, also known as M. balsa mea Wild) is a hybrid mint, formed from a cross between the water mint (Menthe aquatic) and spearmint (Menthe spiced). It is found wild occasionally with its parent species. Peppermint has a high menthol content, and its oil also contains menthone and menthyl esters, particularly menthyl acetate. Dried peppermint typically has 0.3-0.4% of volatile oil containing menthol (29-48%), menthone (20-31%), menthyl acetate (3-10%), menthofuran (1-7%) and many trace constituents including limonene, pulegone, eucalyptol, and pinene. In one embodiment, the peppermint leaf extract is used in concentrations of at least 10:1, and as high as 100:1.

Some of the other transfer agents that have been found to be natural insect repellents include; Achillea alpine, alpha-tyerpinene, basil, callicarpa Americana or Beautyberry, Camphor, castor oil, Catnip, cedar oil, celery extract, cinnamon, clove, fennel, garlic, geranium, lavender, lemongrass, marigold, rosemary and thyme. Of course, these various materials work best when reduced to some oil or concentrate, also in a 10:1 (or higher) concentration.

Simply ingesting the appropriate transfer agent will not be enough in developing an effective ingestible insect repellent system. The challenge is that the metabolism of most humans and animals reacts at different levels, making for an insect repellent that would have many unhappy customers.

In order to maximize said effectiveness, in one embodiment, a catalyst group, comprised of a combination of B vitamins (also known as B-complex vitamins) would be added to the transfer agent described above. B vitamins are a group of water-soluble vitamins that play important roles in cell metabolism. B vitamins were once thought to be a single vitamin, then referred to as vitamin B. Later research showed that they are chemically distinct vitamins, although they often coexist in the same foods. Supplements containing all eight are referred to as a vitamin B complex, while Individual B vitamin supplements are referred to by the specific name of each vitamin (e.g., $B_1$, $B_2$, $B_6$ etc.).

In one embodiment, the transfer agent is combined with one or more B complex catalyst groups, said catalyst groups formed from a combination of individual B vitamins from a group comprised from said vitamin B complex. They have the effect of accelerating the user's metabolism, facilitating the exuding of the transfer agent across the dermis (preferably as part of sweating). In one embodiment, this is done by adding quantities of vitamins $B_1$ (Thiamine), $B_2$ (Riboflavin), $B_6$ (Pyridoxine, pyridoxal, or pyridoxamine, or pyridoxine hydrochloride)) and $B_{12}$ (Cobalamins or Cyanocobalamin).

In one embodiment, the ratios of transfer agent to catalyst group vitamins ($B_1$, $B_2$, $B_6$ and/or $B_{12}$) is in the 1000:1 to 20000:1, with a 7000:1 ratio found to be effective. In effect, the selected B complex catalyst group 'encourages' your body to sweat, something fairly common when encountering mosquitoes, which tend to exist in high humidity environments. Various combinations are possible, with the key being an up to 33% variation in a roughly 1750:1 transfer agent to totality of catalyst group. Various catalyst groups' combinations are possible, with an up to 33% variation on equal parts of $B_1$, $B_2$, $B_6$, and $B_{12}$.

As for their dilution in fluids, the various examples seen below provide an idea of mixing ratios, with the main effect in the amount of fluid being the duration of protection. In general approximately 350 mg of transfer agent diluted in 240 ml, are sufficient for 2 to 6 hours of protection.

In addition to the above B-complex selection, other vitamins and elements may be used to fulfill other human health conditions, such as those comprising, the remaining B-complex members, including $B_3$ (niacin or niacinamide), $B_5$ (Pantothenic acid or Calcium d-Pantothenate), $B_7$ (Biotin) and $B_9$ (Folic Acid), Vitamin C or Ascorbic Acid, as well as stability agents such as Potassium Sorbate in various ratios.

In one embodiment, the invention is made into a premix, for mixing with an appropriate carrier. Such a premix would be optimal when combined with fruit juices (including orange, grapefruit, grape, apple, cranberry, etc.), milk or milk by-products, coffee or tea, soft drinks (carbonated and non-carbonated), water (also carbonated or non-carbonated), sport drinks, and any other human ingestible fluid. In an alternate embodiment, the mix is added to a syrup or other mixer intended for use with alcoholic drinks.

In another embodiment, the mixture is added to a fluid (such as milk or juice) which is then processed using a UHT process. Ultra-high temperature processing, (less often) ultra-heat treatment (both abbreviated UHT), or ultra-pasteurization is the sterilization of food by heating it for an extremely short period, around 1-2 seconds, at a temperature exceeding 135° C. (275° F.), which is the temperature required to kill spores in milk. The most common UHT product is milk, but the process is also used for fruit juices, cream, soy milk, yogurt, wine, and even soups and stews.

Example 1

Composition 1: A premix containing a total of 1850 mg is created, for mixing into an appropriate amount of fluid. Such a premix would contain the following suggested ratios;

| | |
|---|---|
| Lemon extract, 10:1 | 350 mg |
| Biotin | 50 mcg |
| Niacin | 50 mg |
| Pantothenic Acid | 50 mcg |
| Vitamin $B_{12}$ | 50 mcg |
| Vitamin $B_6$ | 50 mcg |
| Vitamin $B_2$ | 50 mcg |
| Potassium Sorbate | 2 mg |

Such a mixture could be mixed with 240 ml of orange juice, providing a refreshing drink capable of repelling insects for two to six hours or longer, depending on a person's metabolism.

Composition Two: A premix containing a total of 925 mg is created, for mixing into an appropriate amount of fluid. Such a premix would contain the following suggested ratios;

| | |
|---|---|
| Peppermint Leaf Extract, 20:1 | 175 mg |
| Biotin | 25 mcg |
| Folic Acid | 25 mcg |
| Niacin | 25 mg |
| Pantothenic Acid | 25 mcg |
| Vitamin $B_1$ | 25 mcg |
| Vitamin $B_{12}$ | 25 mcg |
| Vitamin $B_6$ | 25 mcg |
| Vitamin $B_2$ | 25 mcg |
| Vitamin C | 250 mg |
| Potassium Sorbate | 1 mg |

Such a mixture could be mixed with 120 ml of milk, put through a UHT process, creating a nutritional minimum drink capable of providing in two servings the USDA recommended nutritional minimums, as well as two to six hours of combined protection.

CONCLUSION

In concluding the detailed description, it should be noted that it would be obvious to those skilled in the art that many variations and modifications can be made to the preferred embodiment without substantially departing from the principles of the present invention. Also, such variations and modifications are intended to be included herein within the scope of the present invention as set forth in the appended claims. Further, in the claims hereafter, the structures, materials, acts and equivalents of all means or step-plus function elements are intended to include any structure, materials or acts for performing their cited functions.

It should be emphasized that the above-described embodiments of the present invention, particularly any "preferred embodiments" are merely possible examples of the implementations, merely set forth for a clear understanding of the principles of the invention. Any variations and modifications may be made to the above-described embodiments of the invention without departing substantially from the spirit of the principles of the invention. All such modifications and variations are intended to be included herein within the scope of the disclosure and present invention and protected by the following claims.

The present invention has been described in sufficient detail with a certain degree of particularity. The utilities thereof are appreciated by those skilled in the art. It is understood to those skilled in the art that the present disclosure of embodiments has been made by way of examples only and that numerous changes in the arrangement and combination of parts may be resorted without departing from the spirit and scope of the invention as claimed. Accordingly, the scope of the present invention is defined by the appended claims rather than the forgoing description of embodiments.

We claim:

1. An ingestible composition consisting of:
   38.8% Peppermint leaf extract,
   55.4% Vitamin C,
   5.5% Niacin,
   0.222% Potassium Sorbate; and
   0.0055% of each of Vitamin B1, Vitamin B2, Vitamin B6, Vitamin B12, Pantothethic acid, Biotin and Folic Acid; and
   wherein said composition has the capability of repelling insects.

2. An ingestible composition consisting of a premix and milk; wherein the premix consists of:
   38.8% Peppermint leaf extract,
   55.4% Vitamin C,
   5.5% Niacin,
   0.222% Potassium Sorbate; and
   0.0055% of each of Vitamin B1, Vitamin B2, Vitamin B6, Vitamin B12, Pantothethic acid, Biotin and Folic Acid; and
   wherein said composition has the capability of repelling insects.

3. An ingestible composition consisting of:
   175 mg Peppermint leaf extract,
   250 mg Vitamin C,
   25 mg Niacin,
   1 mg Potassium Sorbate; and
   25 mcg of each of Vitamin B1, Vitamin B2, Vitamin B6, Vitamin B12, Pantothethic acid, Biotin and Folic Acid; and wherein said composition has the capability of repelling insects.

4. An ingestible composition consisting of a premix and milk; wherein the premix consists of:
175 mg Peppermint leaf extract,
250 mg Vitamin C,
25 mg Niacin,
1 mg Potassium Sorbate; and
25 mcg of each of Vitamin B1, Vitamin B2, Vitamin B6, Vitamin B12, Pantothethic acid,
Biotin and Folic Acid; and
wherein said composition has the capability of repelling insects.

5. A method for ingesting a composition, comprising ingesting the composition of any one of claim 1, 2, 3 or 4.

6. A method for making an ingestible composition, wherein the method comprises:
blending ingredients which consist of: 38.8% Peppermint leaf extract, 55.4% Vitamin C, 5.5% Niacin, 0.222% Potassium Sorbate; and 0.0055% of each of Vitamin B1, Vitamin B2, Vitamin B6, Vitamin B12, Pantothethic acid, Biotin and Folic Acid.

7. A method for making an ingestible composition, wherein the method comprises:
blending a premix with milk, wherein the premix consists of: 38.8% Peppermint leaf extract, 55.4% Vitamin C, 5.5% Niacin, 0.222% Potassium Sorbate; and 0.0055% of each of Vitamin B1, Vitamin B2, Vitamin B6, Vitamin B12, Pantothethic acid, Biotin and Folic Acid.

\* \* \* \* \*